United States Patent [19]

Ochoa et al.

[11] Patent Number: 5,316,763
[45] Date of Patent: May 31, 1994

[54] SHORT-TERM ANTI-CD3 STIMULATION OF LYMPHOCYTES TO INCREASE THEIR IN VIVO ACITIVITY

[75] Inventors: Augusto C. Ochoa, Washington, D.C.; Cynthia Loeffler, Woodbury, Minn.; Walter Urba, Gaithersburg; Dan L. Longo, Kensington, both of Md.

[73] Assignees: The United States of America as represented by the Department of Health and Human Services, Washington, D.C.; Regents of the University of Minnesota, Minneapolis, Minn.

[21] Appl. No.: 910,835

[22] Filed: Jul. 10, 1992

Related U.S. Application Data

[63] Continuation-in-part of Ser. No. 728,107, Jul. 10, 1991, abandoned.

[51] Int. Cl.$^5$ ............... A61K 35/14; A61K 45/05; C12N 5/06
[52] U.S. Cl. .................. 424/85.2; 424/93 V; 424/85.8; 435/240.2
[58] Field of Search ............ 424/85.2, 93, 85.8, 424/93 V; 435/240.2; 530/388.22, 388.73

[56] References Cited

U.S. PATENT DOCUMENTS

| | | | |
|---|---|---|---|
| 4,464,355 | 9/1984 | Fabricius et al. | 424/85.2 |
| 4,518,584 | 5/1985 | Mark et al. | 424/85.2 |
| 4,604,377 | 8/1986 | Fernandes et al. | 424/85.2 |
| 4,683,199 | 7/1987 | Palladino | 435/70.4 |
| 4,690,915 | 9/1987 | Rosenberg | 514/2 |
| 4,808,151 | 2/1989 | Dunn, Jr. et al. | 604/6 |
| 4,882,424 | 11/1989 | Schlossman et al. | 530/388.75 |
| 4,908,433 | 3/1990 | Mertelsmann et al. | 530/351 |
| 5,126,132 | 6/1992 | Rosenberg | 424/93 V |

FOREIGN PATENT DOCUMENTS

| | | |
|---|---|---|
| 49611 | 4/1982 | European Pat. Off. |
| 203403 | 12/1986 | European Pat. Off. |
| 336379 | 10/1989 | European Pat. Off. |
| 409655 | 1/1991 | European Pat. Off. |
| WO85/03948 | 9/1985 | PCT Int'l Appl. |
| WO88/00970 | 2/1988 | PCT Int'l Appl. |
| WO89/05657 | 6/1989 | PCT Int'l Appl. |
| WO89/09831 | 10/1989 | PCT Int'l Appl. |
| WO90/04633 | 5/1990 | PCT Int'l Appl. |

OTHER PUBLICATIONS

P. M. Anderson et al., *Cancer Immunol. Immunother.*, 1988, 27, 82.
P. M. Anderson et al., *J. Immunol.*, 1989, 142, 1383.
P. M. Anderson et al., *Cancer Research*, 1990, 50, 1853.
J. A. Aprile et al., *Exp. Hematol.*, 1988, 16, 535 (Meeting Abstract).
C. Aussel et al., *J. Immunol.*, 1987, 138, 3094.
N. Berinstein et al., *J. Immunol.*, 1988, 140, 2839.
C. G. Brooks et al., *J. Immunol.*, 1985, 135, 1145.
M. J. Brunda et al., *Int. J. Cancer*, 1986, 37, 787.
T. H. Corbett et al., *Cancer Research*, 1975, 35, 2434.
L. S. Davis et al., *Cell. Immunol.*, 1989, 118, 208.
H.-A. Fabricius et al., *Immunobiol.*, 1979, 156, 364.
R. I. Fisher et al., *Ann. Int. Med.*, 1988, 108, 518.
J. H. Frenster et al., in *Proc. 5th Leukocyte Culture Conference*, J. E. Harris, ed. (1970), p. 359.

(List continued on next page.)

Primary Examiner—Robert J. Hill, Jr.
Assistant Examiner—David L. Fitzgerald
Attorney, Agent, or Firm—Foley & Lardner

[57] ABSTRACT

The present invention is directed to a method of increasing the in vivo immune response of lymphocytes by stimulating the lymphocytes in vitro in the presence of an anti-CD3 monoclonal antibody for less than about 24 hours to form stimulated lymphocytes; infusing the stimulated lymphocytes into a tumor-bearing mammal; and administering IL-2 to the mammal. As a result of this method, the anti-CD3 stimulated lymphocytes display enhanced immunotherapeutic, e.g., cytotoxicity or lymphokine production, in vivo as represented by a decrease in the number of tumors by at least about 20%.

16 Claims, 7 Drawing Sheets

OTHER PUBLICATIONS

C. J. Froelich et al., *J. Immunol. Meth.*, 1986, 86, 205.
J. Fujita, *Eur J. Cancer Clin.*, 1986, 22, 445.
S. Gallinger et al., *Cancer Research*, 1990, 50, 2476.
T. D. Geppert et al., *J. Clin. Invest.*, 1988, 81, 1497.
E. A. Grimm et al., *J. Exp. Med.*, 1982, 155, 1823.
E. A. Grimm et al., *J. Exp. Med.*, 1983, 158, 1356.
E. A. Grimm et al., *J. Exp. Med.*, 1983, 157, 884.
D. W. Hoskin et al., *Cancer Immunol. Immunother.*, 1989, 29, 226.
K. Itoh et al., *J. Immunol.*, 1985, 134, 3124.
K. Itoh et al., *J. Immunol.*, 1986, 136, 3910.
M. Izquierdo et al., *Clin. Exp. Immunol.*, 1988, 74, 300.
E. M. Janis et al., *Science*, 1989, 244, 713.
G. Jung et al., *Proc. Natl. Acad. Sci. USA*, 1987, 84, 4611.
H. Konno et al., *Chemical Abstracts*, 1989, 110, No. 19, 624, Abstract No. 171523s.
J. Krutmann et al., *J. Investigative Dermatol.*, 1990, 94, 204.
S. S. Kulkarni et al., *Annals of the New York Academy of Sciences*, 1987, 507, 344.
O. Leo et al., *Proc. Natl. Acad. Sci. USA*, 1987, 84, 1374.
M. T. Lotze et al., *Cancer Res.*, 1981, 41, 4420.
M. T. Lotze et al., *J. Surg. Res.*, 1987, 42, 580.
E. Lotzova et al., *Nat. Immun. Cell Growth Regul.*, 1987, 6, 219.
M. Malkovsky et al., *Nature*, 1987, 325, 262.
S. C. Meuer et al., *Proc. Natl. Acad. Sci. USA*, 1984, 81, 1509.
S. Miescher et al., *J. Immunol.*, 1986, 136, 1899.
G. B. Mills et al., *J. Cell. Physiol.*, 1989, 141, 310.
R. P. Moser et al., Int'l. Symp. on Pediatric Neuro-Oncology, Jun. 1–3, 1989, Seattle, Wash., Meeting Abstract No. A14.
J. J. Mule et al., *Science*, 1984, 225, 1487.
L. M. Muul et al., *J. Immunol. Meth.*, 1986, 88, 265.
S. Shu et al., *J. Immunol.*, 1985, 135, 2895.
S. Shu et al. *J. Immunol.*, 1986, 136, 3891.
K. A. Smith, *Science*, 1988, 240, 1169.
P. M. Sondel et al., *J. Immunol.*, 1986, 137, 502.
J. Stankova et al., *FASEB*, 1988, 2, Abstract No. 2114, 72nd Annual Meeting of FASEB, May 1988 (Meeting Abstract).
J. Stankova et al., *Cell. Immunol.*, 1988, 121, 13.
J. L. Strausser et al., *J. Immunol., 1978, 121, 1491.*
L. Tan et al., *Biochemical Society Transactions*, 1989, 17, 693.
R. J. Tatake et al., *Cell. Immunol.*, 1987, 108, 42.
C.-C. Ting et al., *Immunol. Invest.*, 1990, 19, 347.
M. C. Turco et al., *Blood*, 1989, 74, 1651.
R. J. van de Griend et al., *J. Immunol.*, 1987, 138, 1627.
V. von Fliedner et al., *Progress in Chemical and Biological Research: Cellular Immunotherapy of Cancer*, 1987, 244, 223.
B. M. Vose, *Int. J. Cancer*, 1982, 30, 135.
A. Weiss et al., *J. Clin. Immunol.*, 1984, 4, 165.
W. H. West et al., *J. Immunol.*, 1977, 118, 355.
T. L. Whiteside et al., *Int. J. Cancer*, 1986, 37, 803.
J. M. Williams et al., *J. Immunol.*, 1985, 135, 2249.
L. M. Muul et al., *J. Immunol.*, 1987, 138, 989.
A. C. Ochoa et al., *J. Immunol.*, 1987, 138, 2728.
A. C. Ochoa et al., *Cancer Res.*, 1989, 49, 963.
J. R. Ortaldo et al., *Int. J.Cancer*, 1983, 31, 285.
J.-F. Peyron et al., *Biochem. J.*, 1989, 258, 505.
J. L. Platt et al., *J. Exp. Med.*, 1983, 158, 1227.
H. Rabinowich et al., *Cancer Res.*, 1987, 47, 173.
S. A. Rosenberg, *J.N.C.I.*, 1985. 75, 595.
S. A. Rosenberg, in *Important Advances in Oncology*, V. T. DeVita et al., eds., J. P. Lippincott Co., Philadelphia, Pa. (1988) at pp. 217–257.
S. A. Rosenberg et al., *J. Immunol*, 1978, 121, 1951.
S. A. Rosenberg et al., *Adv. Cancer Res.*, 1977, 25, 323.
S. A. Rosenberg et al., *Ann. Int. Med.*, 1988, 108, 853.
S. A. Rosenberg et al., *Ann. of Surg.*, 1988, 208, 121.
S. A. Rosenberg et al., *N. Engl. J. Med.*, 1985, 313, 1485.
S. A. Rosenberg et al., *N. Engl. J. Med.*, 1987, 316, 889.
S. A. Rosenberg et al., *Science*, 1986, 233, 1318.
R. R. Salup et al., *Cancer Immunol. Immunother.*, 1986, 22, 31.
R. Schwab et al., *J. Immunol.*, 1985, 135, 1714.
S. C. Yang et al., *Proc. Annu. Meet. Am. Assoc. Cancer Res.*, 1988, 29, Abstract No. A1603.
Y. P. Yen et al., *Proc. Annu. Meet. Am. Assoc. Cancer Res.*, 1987, 28, Abstract No. 403 (Meeting Abstract).
Y. P. Yen et al., *Proc Annu. Meet. Am. Assoc. Cancer Res.*, 1988, 29, Abstract No. A1616 (Meeting Abstract).
S. Yokota et al., *Fed. Proc.*, 1987, 46, 781 (Meeting Abstract).
I. Yron et al., *J. Immunol.*, 1980, 125, 238.
J. M. Zarling et al., *Nature*, 1978, 274, 269.
J. M. Zarling et al., *Cancer Immunolo. Immunother.*, 1983, 15, 237.
J. L. Platte et al., *J. Exp. Med.*, 1982, 157, 17.
Y.-S. Yun et al., *Cancer Res.*, 1989, 49, 4770.
Tsoukas et al., "Activation of Resting T Lymphocytes By Anti-CD3 (T3) Antibodies in the Absence of Monocytes", The Journal of Immunology, vol. 135, No. 3, Sep. 1985, pp. 1719–1723.
Hogan et al., "Lymphokine-Activated and Natural Killer Cell Activity in Human Intestinal Mucosa, The Journal of Immunology, vol. 135, No. 3, Sep. 1985, pp. 1731–1738.

SHORT-TERM ANTI-CD3 STIMULATION OF LYMPHOCYTES TO INCREASE THEIR IN VIVO ACITIVITY

CROSS REFERENCE TO RELATED APPLICATION

This application is a continuation-in-part of U.S. patent application Ser. No. 07/728,107, filed Jul. 10, 1991, now abandoned.

FIELD OF THE INVENTION

The present invention relates to the culturing of lymphocytes in the presence of a lymphocyte surface receptor antibody so as to elicit an immune response in vivo. Specifically, it relates to the short-term stimulation of lymphocytes in vitro with anti-CD3 monoclonal antibody followed by the reintroduction of the activated lymphocytes in vivo. The invention is particularly represented by improved antitumor activity.

BACKGROUND OF THE INVENTION

T lymphocytes, i.e., T cells, are central players in the immune response by virtue of their ability to recognize antigens with a high degree of specificity, to act as effector cells in the lysis of specific target cells, and to regulate the nature and intensity of the immune response. Once research clarified the role of T lymphocytes in the immune system, it became useful to stimulate selected lymphocyte populations and subpopulations that could play a role in immune responses, especially in response to tumors.

Interleukin-2 (IL-2), a lymphokine produced by helper T cells, stimulates the growth of T cells and NK cells that bear IL-2 receptors, either in vivo or in vitro. The in vitro incubation of resting lymphocytes in media containing IL-2 for three to four days induces the generation of lymphocytes capable of lysing fresh tumor cells, but not normal cells. These lymphocytes are referred to as lymphokine activated killer (LAK) cells. See, for example, I. Yron et al., *J. Immunol.*, 238 (1980); M. T. Lotze et al., *Cancer Res.*, 41, 4420 (1981); and S. A. Rosenberg et al., *Natl. Cancer Inst.*, 75, 595 (1985). This ability of IL-2 to induce the proliferation of lymphocytes with immune reactivity and with the ability to lyse fresh autologous, syngeneic, or allogeneic natural killer (NK) cell resistant tumor cells, but not normal cells, has resulted in further developments in the area of adoptive immunotherapy, i.e., cell transfer therapies.

Typical adoptive immunotherapy involves the administration of immunologically active cells to an individual for the purpose of providing a beneficial immunological effect to the individual, e.g., reduction or control of cancerous or diseased tissue. These immunologically active cells, e.g., lymphokine-activated killer cells and tumor infiltrating cells, are typically taken either from the individual to be treated, known as an autologous treatment, or from another individual, known as an allogenic treatment. Lymphokine-activated killer cells are typically taken by venipuncture or leukophereses. Tumor infiltrating cells are taken from tumors removed during surgery. The lymphocytes are cultured to increase their number and activate their antitumor activity, and infused back into the patient. Thus, the majority of conventional efforts in adoptive immunotherapy are directed at increasing the number of activated cells in vitro followed by infusion back into the patient.

Animal experiments transferring immunologically active cells, e.g., LAK cells, from healthy animals to animals with cancerous tumors have suggested that adoptive immunotherapy can elicit an antitumor effect in certain tumor models with a high degree of effectiveness. Furthermore, the administration of IL-2 in addition to LAK cells has proven effective in the treatment of a variety of murine malignancies. IL-2 also leads to the in vivo proliferation of transferred LAK cells. These initial animal studies were repeated with humans in clinical trials.

The human studies demonstrated that LAK cells plus IL-2, or IL-2 alone, can be effective in mediating the regression of established metastatic cancer in selected patients. See, for example, S. A. Rosenberg, "Immunotherapy of Patients with Advanced Cancer Using Interleukin-2 Alone or in Combination With Lymphokine Activated Killer Cells" in *Important Advances in Oncology* 1988, J. B. Lippincott Co., 217, (1988).

Although adoptive immunotherapy has met with certain success, a difficulty with many of the experimental protocols is that a large number of cells is required in the therapy. Furthermore, conventional protocols have proven less than desirable because of the large amount of culture medium, the large amount of IL-2, the large number of hours involved in culturing cells to develop LAK activity, the time involved in clinical treatment, and the side effects of treatment. The infusion of LAK cells also frequently results in the development of respiratory difficulty. These cells are large and sticky and bind to the vascular system in the lungs causing severe damage that can result in the patient requiring intensive care management.

To overcome some of these difficulties, advances have been made to improve the in vitro culturing process. For example, T cells cultured in the presence of IL-2 and monoclonal antibodies (MoAb) against the antigen receptor complex CD3, i.e., anti-CD3 MoAb, have been found to proliferate and demonstrate LAK activity on a per cell basis. See, for example, P. M. Anderson et al., *Cancer Immunol. Immunother.*, 27, 82 (1988); P. M. Anderson et al., *J. Immunol.*, 142, 1383 (1989); and A. C. Ochoa et al., *Cancer Res.*, 49, 963 (1989).

Some efforts have been aimed at activating in vivo antitumor mechanisms; however, there has been limited success in this area. For example, patients have received high doses of IL-2 with significant toxicity. The direct infusion of anti-CD3 monoclonal antibody alone induces nonspecific antitumor function in mice. See, for example, D. W. Hoskin et al., *Cancer Immunol. Immunother.*, 29, 226 (1989). Based on the positive results in murine models, direct infusion of anti-CD3 MoAb has been attempted in humans. Although patients who have directly received the anti-CD3 MoAb OKT3 have experienced the activation of some T cells in vivo. the toxicity of intravenous OKT3 reaches the maximum tolerated dose (MTD) before immune efficacy develops. It is believed that the free OKT3 is responsible for the majority of these toxic effects. In addition, the infusion of anti-CD3 induces the production of endogenous antibodies which neutralize the effect of the anti-CD3 thus complicating the possibility for repeated therapy.

Although direct infusion of anti-CD3 results in significant levels of toxicity, cells activated by anti-CD3 outside of the body are useful in adoptive immunotherapeutic techniques. Anti-CD3 induces, at least in part, activation of tumoricidal T cells as well as activated NK (LAK cells). Conventional IL-2 therapy, however, only activates LAK cells. Furthermore, some studies have shown that certain tumor target cells are more susceptible to anti-CD3 activated T cells than LAK cells. See, for example, J. Stankova et al., *Cell. Immunol.*, 121, 13 (1989).

A comparison of the efficacy of cells stimulated with IL-2 for four days, with anti-CD3 for 72 hours, as well as the antitumor activity induced by the direct infusion of anti-CD3 MoAb has been undertaken. See, for example, S. Gallinger et al., *Cancer Res.*, 50, 2476 (1990). It has been determined that in this murine model the most effective way of reducing tumor is direct infusion of anti-CD3. Infusion of cells stimulated with anti-CD3 was less effective while infusion of cells cultured in IL-2 was least effective.

It has been shown that anti-CD3 induced effector cells acquire cytolytic activity in vitro within 24 hours of incubation of murine lymphocytes with anti-CD3. It has also been shown that in vitro incubation of peripheral blood lymphocytes of normal donors with the anti-CD3 monoclonal antibody OKT3 for 45 minutes resulted in the acquisition of lytic activity against fresh leukemic cells. See, E. Lotzova et al., *Nat. Immun. Cell Growth Regul.*, 6, 219 (1987). It is generally believed, however, that for effective in vivo activity, cells must be incubated with anti-CD3 for at least about 72 hours.

Thus, conventional methods of activating cells in vitro or in vivo have not to date successfully eliminated the need for convenient, effective, and safe therapeutic methods. In general, conventional methods require the development of immunotherapeutic function, e.g., lytic activity, in cells before they are used in adoptive immunotherapy. Because of this limitation, culturing of cells can last for several days before they can be infused back into a patient. A need therefore exists for a more convenient, less time consuming, and more efficient method of culturing cells. That is, a need exists for a method of producing lymphocytes capable of proliferation and enhanced immunotherapeutic efficacy that: (1) is not time consuming; (2) is less expensive; (3) has fewer, if any, side effects; (4) is simple and convenient; and (5) does not require prolonged in vitro culture.

SUMMARY OF THE INVENTION

The present invention is directed to a method of enhancing the in vivo immune response, i.e., the immunotherapeutic activity, of lymphocytes. This method includes the steps of stimulating the lymphocytes in vitro in the presence of an anti-CD3 monoclonal antibody alone for less than about 24 hours to form stimulated lymphocytes, infusing the stimulated lymphocytes into a tumor-bearing mammal, and administering an effective amount of IL-2 to the mammal. The stimulation of lymphocytes in vitro can be done in the presence of low doses of IL-2 (<300 units/ml), in contrast to high doses and long exposure as was practiced in the prior art. As a result of this method, the anti-CD3 stimulated lymphocytes display enhanced immunotherapeutic efficacy, e.g., cytotoxicity or production of lymphokines, in vivo as represented by a decrease in the tumor burden by at least about 20%. Preferably, the short-term stimulation of the lymphocytes occurs over a period of about 12–18 hours, more preferably less than 4 hours, and as short as 30 minutes, and the tumor burden is decreased by at least about 40%, more preferably by at least about 60%, and most preferably by at least about 80%.

DETAILED DESCRIPTION

As used herein, "stimulating" or "culturing" indicates the process whereby cells are placed in a tissue culture medium comprising nutrients to sustain the life of the cells, and other additives, such as the antiCD3 monoclonal antibody. Stimulation can be done in the presence of IL-2 but generally IL-2 is not included. If stimulation of lymphocytes is to be done in the presence of IL-2, low doses of IL-2 (<300 units/ml) are used in contrast to the high and long exposure as was practiced in the prior art. This process can take place in any vessel or apparatus. The process can involve various stages of culturing and subculturing. However, typically, only one culturing or stimulating step is desirable. IL-2 activity is expressed herein in Hoffmann-LaRoche units. 0.2.3 Hoffmann-LaRoche units equal International Units.

As used herein, "immune response" or "immunotherapeutic activity" includes antitumor activity, such as lymphokine production, specific lytic activity, or the nonspecific ytic activity of lymphokine activated killer (LAK) cells and natural killer (NK) cells. Furthermore, as used herein "antitumor activity" includes a reduction in the number of tumors as well as a reduction in the size of tumors which can be collectively referred to as reduction in tumor burden.

As used herein "lymphocytes" include T cells, such as CD3 T cells including CD4+ and CD8+ cells. It is understood that this includes tumor infiltrating lymphocytes (TIL cells). Preferably, the lymphocytes are T cells.

It has been discovered that lymphocytes can be stimulated in vitro with an antibody to a lymphocyte surface receptor, without the presence of IL-2, for short periods of time, i.e., for less than about 24 hours, preferably for about 12-18 hours and as short as 30 minutes. These cells have a high therapeutic efficacy upon in vivo injection. The anti-CD3 stimulated cells are less toxic and are generally smaller in size than cells cultured only in IL-2 for several days. Reduced pulmonary toxicity may be due to the smaller size of anti-CD3 stimulated cells which presumably circulate more freely through the vascular system than larger LAK cells. Similarly, because the anti-CD3 stimulated cells can multiply in number in the presence of IL-2, small numbers of injected anti-CD3 stimulated cells can proliferate to large numbers following in vivo exposure to IL-2 allowing for the administration of fewer cells.

The antibody to a lymphocyte surface receptor can be any of a variety of monoclonal antibodies (MoAb) against a surface antigen receptor complex having mitogenic potential. For example, it can be an anti-CD3, anti-CD2, anti-CD4, anti-CD28, anti-CD11$b$, etc., MoAb. It is preferably an anti-CD3 MoAb. The anti-CD3 MoAb used to stimulate human T cells can be, but is not limited to, OKT3, WT32, Leu-4, SPV-T3c, RIV9, 64.1, etc. The anti-CD3 MoAb used to stimulate murine T cells is more preferably the anti-murine CD3 MoAb 145-2C11, which has been identified by O. Leo et al., *Proc. Natl. Acad. Sci. USA*, 84, 1374-1378 (1978), and is available from American Type Culture Collection (ATCC). Mouse anti-human OKT3 is available from the Ortho Division of Johnson and Johnson.

Cells treated with anti-CD3 MoAb for less than about 24 hours are preferably treated with a total dose of about 0.1 ng/ml to 10 ng/ml anti-CD3 antibody, in stimulating one whole leukopheresis. A "leukopheresis" is defined as the peripheral blood lymphocytes (PBLs) enriched for mononuclear cells removed during the course of a standard pheresis procedure. More preferably, antiCD3 is used in a total dose of about 10 ng/ml used in stimulating one whole leukopheresis.

The anti-CD3 stimulation induces the expression of the IL-2 receptor. These cells are then collected and placed in the body of an organism, preferably a mammal, such as a mouse or a human, where they develop immunotherapeutic activity or lymphokine production, e.g., cytotoxic activity or lymphokine production, upon the administration of IL-2. More preferably the cells are placed in the body of a human for immunotherapeutic treatment.

Because cells stimulated for a short period of time with anti-CD3 in vitro are smaller than cells cultured for 4 days in IL-2, or IL-2 in conjunction with anti-CD3, and because they have not had time to develop lytic activity, they are less toxic when administered in vivo. The administration to mice of large numbers ($>50\times10^6$) of cells stimulated with IL-2, or IL-2 and anti-CD3, and cultured for greater than 4 days can produce acute respiratory problems in mammals due to sludging, i.e., stasis or blocking the lung capillaries, by these large cells in pulmonary capillaries. In contrast, stimulation of cells with anti-CD3 alone or anti-CD3+IL-2 for less than 24 hours does not generally produce an increase in the size of the cells. Furthermore, cells stimulated overnight with anti-CD3 proliferate, i.e., multiply, in vivo when administered into an animal receiving IL-2. Therefore, smaller numbers of cells can be administered.

With the administration of an effective amount of IL-2 in vivo, the cells display an enhanced proliferation and antitumor activity. The administration of IL-2 preferably occurs over a period of about 7 days. The amount of IL-2 effective for enhancing cell proliferation and antitumor activity in vivo, such that there is at least about a 20% decrease in the number of tumors, depends on the mammal being treated. For example, about 10,000-70,000 units/day of IL-2, preferably about 50,000 units/day of IL-2, are administered to mice, and about $1 \times 10^6$ to $6\times 10^6$ International Units/m$^2$/day are administered to humans.

As stated above, it is preferred that the cells are initially stimulated for less than 24 hours with anti-CD3 MoAb. While it is within the scope of the invention to initial culture, if desired, it is more efficient to stimulate cells with anti-CD3 MoAb alone, collect the stimulated cells, infuse the stimulated cells into a tumor-bearing mammal, and then administer IL-2 to the mammal.

Typically, the antitumor activity of the anti-CD3 cells stimulated in vitro is increased in vivo upon the administration of IL-2 by about 20%, preferably by about 50%, more preferably by about 60%, and most preferably by about 80%. Alternatively stated, the anti-CD3 stimulated lymphocytes display enhanced immunotherapeutic activity, e.g., cytotoxicity or lymphokine production, in vivo as represented by a decrease in the tumor burden by at least about 20%, preferably by at least about 40%, more preferably by at least about 60%, and most preferably by at least about 80%. For example, in a typical protocol untreated animals will usually develop greater than about 250 tumors, while animals treated with anti-CD3 stimulated cells and IL-2 will usually develop less than about 40 tumors.

Similar activity can result from cells stimulated in vitro with anti-CD3 for less than about 4 hours, and even for as short as 30 minutes. The proliferation and antitumor activity of these cells can occur not only in mice, but also in humans.

The tumors which have shown a reduction upon treatment with cells stimulated by the method of the present invention and IL-2 include MCA-38 (colon carcinoma), RENCA (renal cell carcinoma), MCA-102 (sarcoma) which are all derived from different embrionary origins. The colon carcinoma is derived from the ectoderm (the origin of the lining of all organs as well as the skin), the renal cell carcinoma is derived from the neural crest (origin of nervous tissue, gonads and adrenal glands), and the sarcoma is derived from the connective tissue (bone, ligaments). Therefore, it is expected that other tumors from a similar origin will respond to therapy. None of the tumors tested in vitro up to now have been resistant to cytolysis by T-AK cells which have been expanded in IL-2.

T lymphocytes can also function as suppressor cells, i.e., they have regulatory mechanisms by which they can stop an on-going immune response. Therefore, it is expected that some of the T lymphocytes activated during the preparation of T-AK cells will be useful in the treatment of diseases where the immune response produces damage to normal tissues, e.g., autoimmune diseases such as Lupus erythematosus, multiple sclerosis, rheumatological conditions (rheumatoid arthritis), allergic conditions, and the rejection of transplanted organs such as kidney, liver, heart, lung, or bone marrow (autologous or allogeneic).

The interleukin-2 is a commercially available T cell growth factor. It can be a naturally occurring IL-2, such as might be derived from cultured rat splenocytes, or it can be recombinant IL-2. It is believed that other lymphokines can also be used in the present invention either in low doses together with anti-CD3 in vitro or administered to the patient following infusion of anti-CD3 stimulated lymphocytes. These include IL-1, IL-4, IL-6, interferon, etc. It is envisioned that they can be used alone, in sequence, or in combination with IL-2 as an adjunct to primary anti-CD3 stimulation.

Although free IL-2 can be used in the method of the invention, the IL-2 is preferably incorporated into liposomes as a delivery system. These phospholipid vesicles can contain varying amounts of IL-2, or other cytokines or bioactive compounds, depending on the type of interaction between the solute and the phospholipid.

Many methods have been proposed for the preparation of liposomes. Most of these methods involve a form of aqueous hydration of the lipid, which may be either in a powdered form or as a dried film. One of the most widely used techniques is known as the film method. Briefly, lipids of the desired composition in solution with an organic solvent are dried in the form of a thin film on the walls of a round-bottomed flask. A bioactive compound can be included in the film at this stage. The dry film is hydrated by adding a suitable aqueous phase and gently swirling the flask. With a hydrophilic bioactive compound, an aqueous solution is used for hydration. The liposomes formed by this procedure generally have a number of concentric bilayers and are called multilamellar vesicles (MLVs).

The liposomal IL-2 used in the present invention is preferably prepared using dimyristoyl phosphatidyl choline (DMPC, Avanti Polar Lipids, Pelham, AL). Liposomes were formulated utilizing a freeze/thaw and bath sonication technique, according to the method described by P. M. Anderson et al., *Cancer Research*, 50, 1853–1856 (1990).

Several routes of administration can be used for the administration of liposomes, for example, intravenous, subcutaneous, intraperitoneal, and oral delivery. An important advantage of liposomal delivery is the change in tissue distribution and binding properties as compared to the free forms of the bioactive ingredient, resulting in enhanced therapeutic index and decreased toxicity.

The following examples are set forth as representative of specific and preferred embodiments of the present invention. These examples are not to be construed as limiting the scope of the invention in any manner. It should be understood that many variations and modifications can be made while remaining within the spirit and scope of the invention.

EXAMPLE 1

Tumor Preparation and Tumor Cell Lines

The murine tumor cell line, MCA-38, a weakly immunogenic murine colon adenocarcinoma, was induced by the subcutaneous (s.c.) injection of dimethylhydrazine in C57BL.6 mice according to the method of T. H. Corbett et al., *Cancer Research*, 35, 2434–2439 (1975), which is incorporated herein by reference. A MCA-38 tumor cell line was established in tissue culture media (TCM) with 10% fetal calf serum (FCS, available from GIBCO Laboratories, Grand Island, N.Y.) and used as a target for subcutaneous (s.c.) passage in C57BL.6 mice. The TCM by consisted of Rosewell Park Memorial Institute (RPMI) 1640 medium (obtained from GIBCO), supplemented with 25 mM HEPES [N-(2-hydroxyethyl)piperazine-N'-(2-ethanesulfonic acid) (available from GIBCO Laboratories), 2 mM L-glutamine (available from GIBCO Laboratories), and 100 units/ml penicillin (GIBCO), 100 μg/ml streptomycin (GIBCO). The cell line was maintained in tissue culture media.

EXAMPLE 2

Preparation of IL-2 in Liposomes

Liposomes containing IL-2 for use in all Examples were prepared as follows. IL-2 (specific activity $1.5 \times 10^7$ units/mg Hoffmann-LaRoche, Inc., Nutley, N.J.) containing 25 mg human serum albumin per $1 \times 10^6$ units IL-2 was diluted in Hanks' Balanced Salt Solution (HBSS, obtained from GIBCO Laboratories, Grand Island, N.Y., also available from SIGMA Chemical Co., St. Louis, Mo.) and added to dimyristoyl phosphatidyl choline (DMPC, Avanti Polar Lipids, Pelham, Ala.). Liposomes were formulated utilizing a freeze/thaw and bath sonication technique, according to the method described by P. M. Anderson et al , *Cancer Research*, 50, 1853–1856 (1990), which is incorporated herein by reference. To standardize the quantity of lipid injected with each concentration of IL2 tested, IL-2 liposomes were synthesized utilizing a constant ratio of lipid:IL-2 solution of 15 mg DMPC:0.2 ml IL-2 solution. Mice treated with IL-2 liposomes received $5.0 \times 10^4$ units IL-2 liposomes. No liposomes were used in the human studies, however.

EXAMPLE 3

Cells Stimulated with Anti-CD3 In Vitro and Their Effect on Hepatic Tumors In Vivo Peripheral blood lymphocytes, or splenocytes, from C57BL.6 mice were obtained by extracting the spleen and crushing it with a glass stopper in a petri dish with HBSS. A single suspension was created by repeated pipetting. The splenocytes were purified over Ficoll-Hypaque, (Pharmacia, Piscataway, N.J.), washed twice in phosphate buffered saline (PBS, pH 7.4 available from GIBCO, Grand Island, N.Y.) and placed in culture in RPMI 1640 with 5% fetal calf serum, and 2% by volume of antiCD3 supernatant 145-2C11 at a concentration of $2 \times 10^6$ cells/ml Without IL-2 (anti-murine CD3 MoAb 145-2C11, which has been identified by O. Leo et al., *Proc. Natl. Acad. Sci. USA*, 84, 1374–1378 (1978), is available from ATCC). Cells were harvested the next morning, washed 3 times in HBSS, and resuspended in HBSS prior to intravenous injection. The concentration of anti-CD3 in the supernatant of 145-2C11 hybridoma is approximately 1–2 micrograms/ml.

For comparison purposes, splenocytes were stimulated with anti-CD3 (145-2C11) and IL-2 (100–300 units/ml) in the following manner. Cells were separated by FicollHypaque, washed 3 times in PBS, and placed at $1-2 \times 10^6$ cells/ml in RPMI 1640+5% fetal calf serum+2% by volume anti-CD3 (145-2C11). The cells were diluted every 48–72 hours such that the concentration of cells was maintained at approximately $1 \times 10^6$ cells/ml. The cells injected into mice were harvested on day 3 and 5 of culture.

Approximately 20 million cells treated either with the anti-CD3 MoAb alone, or with the anti-CD3 MoAb and IL-2, were injected intraveneously (i.v.) into C57BL.6 mice bearing hepatic tumors of MCA-38 colon adenocarcinoma. Both groups of mice received IL-2 in liposomes (50,000 units/day) intraperitoneal (i.p.) for five days. The number of hepatic tumors were determined on day 14 by double blind counting of surface tumors. The results are listed below in Table 1. These results demonstrate that cells stimulated with anti-CD3 for only 18 hours in vitro will develop antitumor activity in vivo in the presence of IL-2. The antitumor activity is comparable to that of cells cultured in vitro in anti-CD3+IL-2 for 3-5 days.

TABLE 1

Effect of Adoptive Cells and IL-2 Liposomes on Number of Hepatic Tumors

| Mouse | Anti-CD3 Alone for 18 hrs. | Anti-CD3 + IL-2 for 3-5 days |
| --- | --- | --- |
| 1 | 72 | 89 |
| 2 | 59 | 72 |
| 3 | 61 | 68 |
| 4 | 57 | 51 |
| 5 | 43 | 47 |
| 6 | 37 | 33 |
| 7 | 10 | 24 |
| 8 | 5 | 15 |
| 9 | 0 | 6 |
| Mean | 38.2 | 45 |
| Median | 43 | 47 |
| Sd | 26.9 | 27.9 |
| Se[1] | 8.9 | 9.3 |

[1] Both groups show equivalent antitumor activity in vivo.

EXAMPLE 4

Cells Stimulated with Anti-CD3 In Vitro and Their Effect on Hepatic Tumors In Vivo Lymphocytes obtained from murine spleens, as described above in Example 3, were stimulated with the anti-CD3 monoclonal antibody 145-2C11 overnight, i.e for approximately 12-18 hours as described above in Example 3.

Approximately 15 million of these cells were injected intravenously (i.v.) into C57BL.6 mice bearing hepatic tumors of MCA-38 colon adenocarcinoma. The mice also received IL-2 in liposomes (50,000 units/day) intraperitoneal (i.p.) for five days. The number of hepatic tumors were determined on day 14 as described above in Example 3.

The controls were C57BL.6 mice injected with tumor cells in a similar manner as the treated mice; however, these mice were treated with IL-2 liposomes (50,000 units/day) only. The results are listed below in Table 2. These results demonstrate that with as little as 15 million cells stimulated for 24 hours with anti-CD3, there is a significant reduction in the number of hepatic tumors.

TABLE 2

Effect of 15 Million Adoptive Cells and IL-2 Liposomes on Number of Hepatic Tumors

| Mouse | Controls | Anti-CD3 |
| --- | --- | --- |
| 1 | 246 | 51 |
| 2 | 231 | 62 |
| 3 | 241 | 34 |
| 4 | 211 | 48 |
| 5 | 234 | 21 |
| 6 | 251 | 31 |
| 7 | 235 | 26 |
| 8 | 219 | 38 |
| 9 | 232 | 27 |
| 10 | 201 | 19 |
| Mean | 230.1 | 35.7 |
| Sd | 15.6 | 14.0 |
| Se | 4.9 | 4.4 |
| p (unpaired student T test) | | 0.001 |

EXAMPLE 5

Titration of CD3 Stimulated Cells Intravenously

Splenocytes, obtained as described above in Example 3, were stimulated with OKT3 and IL-2 as described above in Example 3.

Nine week old C57BL.6 female mice (Harlan) bearing hepatic tumors of MCA-38 colon adenocarcinoma were divided into seven groups. The mice in the three groups intravenously received 5 million, 10 million, or 20 million cells stimulated with anti-CD3 and cultured in the presence of 100 units/ml IL-2 on days 3 and 5. All mice, including a control group, which did not receive adoptively transferred cells, received 50,000 units IL-2 liposomes intraperitoneal qd., i.e., everyday, on days 3-7. For the mice in each of the groups that received adoptively transferred cells, the number of hepatic tumors were determined on day 14 as described above in Example 3. The results are presented below in Table 3. These results demonstrate that there is a distinct correlation between the quantity of cells administered and the number of tumors the mice develop. The mice receiving more cells developed fewer tumors.

This finding is important because a controlling factor in the infusion of cells is the culturing time. Cells cultured for a long period of time increase in size and produce respiratory complications and even death when infused. The stimulation of the cells for less than 24 hours, however, does not induce changes in size, making the cells virtually nontoxic during the administration.

TABLE 3

Titration of CD3 Stimulated Cells Intravenously

| Mouse | Controls | 5 Million | 10 Million | 20 Million |
| --- | --- | --- | --- | --- |
| 1 | 300 | 182 | 94 | 20 |
| 2 | 300 | 300 | 88 | 17 |
| 3 | 302 | 300 | 107 | 0 |
| 4 | 300 | 169 | 74 | 7 |
| 5 | 300 | 75 | 62 | 38 |
| 6 | 300 | 155 | 153 | 21 |
| 7 | 300 | | 123 | 60 |
| 8 | | | 94 | 38 |
| 9 | | | 74 | |
| Mean | 300 | 196.8 | 96.6 | 25.1 |
| Median | 300 | 175.5 | 94.0 | 20.5 |
| Sd | 0.756 | 88.2 | 28.0 | 19.3 |
| Se | 0.286 | 36.0 | 9.3 | 6.8 |

EXAMPLE 6

Preparation of T-AK Cells for T Cell Infiltration Experiment

C57BL.6 murine splenocytes were harvested and activated with anti-murine CD3 MoAb 145-2C11 and interleukin-2 (IL-2,) as described by P. M. Anderson et al., *J. Immunol.*, 142, 1383-1394 (1989), which is incorporated herein by reference. The IL-2 used had a specific activity of $1.5 \times 10^7$ units/mg, and is available from Hoffmann-LaRoche. Fresh splenocytes were incubated in culture flasks at a concentration of $1.0 \times 10^6$ cells/ml of tissue culture media (TCM). The TCM consisted of RPMI-1640, supplemented with 25 mM HEPES [N-(2-hydroxyethyl)piperazine -N'-(2-ethanesulfonic acid)], 2 mM L-glutamine, 5% fetal calf serum, 100 units/ml penicillin, 100 $\mu$g/ml streptomycin, 10 mM nonessential amino acids (Gibco), 100 mM sodium pyruvate (Gibco, Grand Island, N.Y.), and 25 $\mu$M 2-mercaptoethanol (Sigma Chemical Co., St. Louis, Mo.).

To generate T-activated killer cells, i.e., T-AK cells, 2 $\mu$g of 145-2C11 MoAb was added per one ml of TCM. In addition, IL-2 was added to the TCM at a concentration of 100 units/ml. Anti-CD3 MoAb was added only at the start of the culturing process. All cultures were supplemented with fresh TCM containing IL-2 to produce a cell density of $0.2-0.5 \times 10^6$ cells/ml every two to three days. Cultures were sampled on days 3, 5, 7, and 9; cell viability and increases in cell number were determined by the commonly used trypan blue exclusion procedure. Cells utilized in the adoptively transferred T cell infiltration experiment were from day 5, 7, and 9 of culture.

EXAMPLE 7

Adoptively Transferred T Cells Infiltrate MCA-38 Hepatic Tumors

The ability of adoptively transferred T cells with cytolytic activity (T-AK cells) to infiltrate MCA-38 hepatic tumors was evaluated using congenic mice. T-AK cells were generated from splenocytes of C57BL.6 mice that express Thy 1.2 on their lymphocytes, as described in Example 8. Mice of the congenic strain B6:PL-Thy-1$^a$/Cy (available from Frederick Cancer Research Center and Development) that express Thy 1.1 on their T cells were inoculated with MCA-38 and then treated with T-AK cells from Thy1.2 mice (C57BL.6), IL-2 liposomes prepare as described above in Example 2, or a combination of IL-2 liposomes and T-AK cells.

Liver tissue was collected every 48 hours beginning the day after therapy was started (day 4 post tumor inoculation), and evaluated for the number of Thy 1.2+ cells, Lyt.2.2+ cells, L3T4+ cells, and Mac 1+ cells infiltrating the hepatic tumors. Ethidium bromide was added to facilitate identification of the early micrometastases within the liver, according to the method of J. L. Platt et al. described in *J. Exp. Med.*, 157, 17 (1982). Tetraethyrhodamine isothiocyanate conjugated rabbit antiserum to human basement membrane (TRIC) was used to allow differentiation of intravascular cells from infiltrating cells, according to the method of J. L. Platt et al. described in *J. Exp. Med.*, 158, 1227 (1983).

Monoclonal anti-bodies were purified from ascites utilizing saturated ammonium sulfate, washed twice with 50% ammonium sulfate, dialyzed against PBS, and adjusted to a final concentration of 500 $\mu$g/ml in PBS. The antibody recognizing the cell marker Lyt.2 is 2.43 (ATCC Cat. No. TIB 210), and that recognizing the cell marker L3T4 is GK1.5 (ATCC Cat. No. TIB 207). Rat anti-Thy 1.2 FITC was obtained from Becton Dickinson (Mountain View, Calif.) and anti-MAC-1 from Boehringer Mannheim (Indianapolis, Ind.).

Figure 1A:
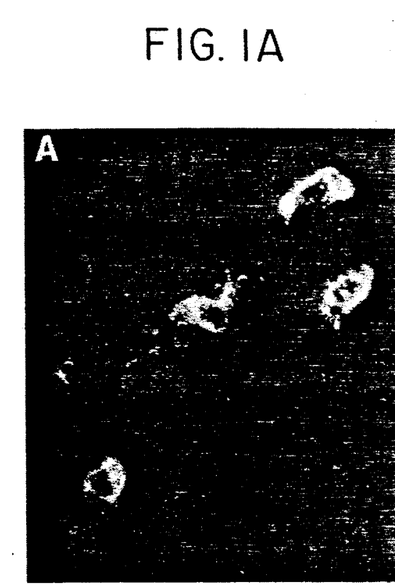
FIG. 1 illustrates the infiltration of murine hepatic tumors with activated lymphocytes stimulated with anti-CD3 and cultured with IL-2. (A) Lyt.2+ cells infiltrating hepatic metastases 48 hours after infusion of IL-2 liposomes alone; (B) Thy1.2+ cells infiltrating metastases 48 hours after infusion of Thy1.2+ T-AK cells into congenic Thy1.1 tumor bearing mice; (C) Lyt.2+ cells infiltrating tumor 48 hours after combination of IL-2 liposomes and adoptive immunotherapy; (D) solitary Lyt.2+ cell in untreated control mouse.
Figure 1B:
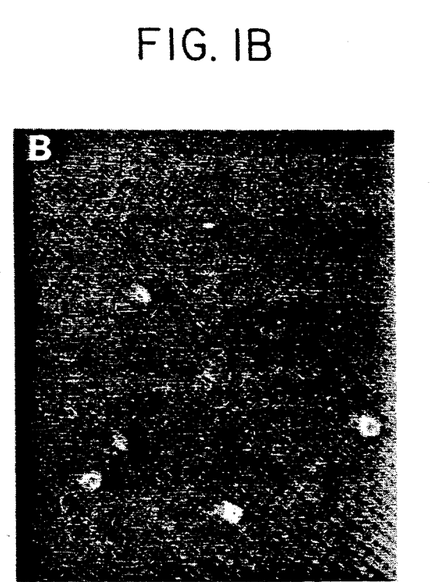

As seen in FIG. 1a, mice treated with IL-2 liposomes alone demonstrated host Lyt.2+ cells infiltrating the hepatic tumors within 24 hours of i.p. injection. The number of infiltrating lymphocytes increased over the subsequent 48 hours and remained constant thereafter. A much smaller number of Mac 1+ cells (including both PMNs and monocytes) also infiltrated the tumors of these mice. Rare L3T4+ cells were also noticed. T-AK cells (Thy1.2+) infused without IL-2 liposomes into Thy 1.1+ mice were observed in the tumors two days after initial injection. Rare Mac 1+ cells were also observed, however, no L3T4+ cells were observed.

Figure 1C:
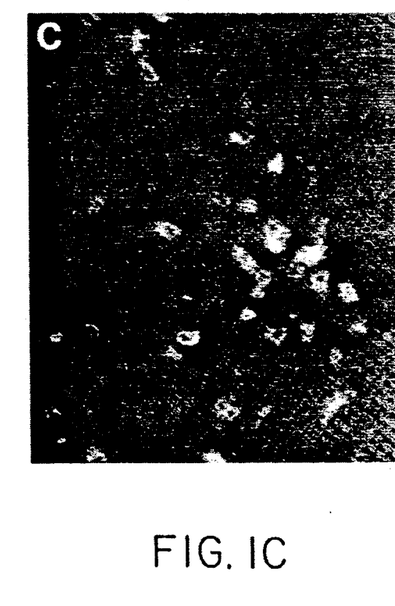
Figure 1D:
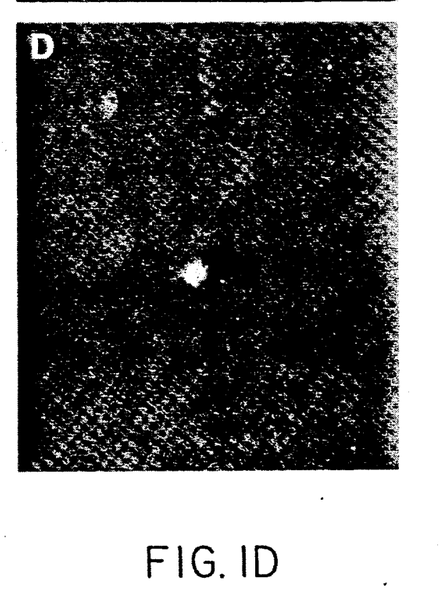

When T-AK cells were administered with IL-2 liposomes, large numbers of Lyt.2+ cells were noted in the tumors. Of these, approximately 60% Thy 1.2+ represented adoptively transferred cells, while 40% were of host origin, as shown in FIG. 1c. These cells were apparent 48 hours after therapy began. A moderate number Mac 1. cells were seen but only rare L3T4+ cells were found. The cellular infiltrate was present up to day 11 of protocol (3 days after the end of therapy) when the mice were sacrificed.

EXAMPLE 8

In Vivo Growth of Anti-CD3 Activated Cells

The data presented in Table 4 demonstrate that the cells activated with anti-CD3 overnight (T-activated killer cells; T-AK) will proliferate in vivo. C57BL.6 mice were injected intravenously with $15 \times 10^6$ anti-CD3 activated cells obtained from B6:PL Thy-1$^a$/Cy mice. These two groups differ in only one genetic characteristic, i.e. they are congenic strains, and therefore, do not reject each other's tissues. However, this genetic characteristic allows the determination of the origin of the lymphocytes proliferating in vivo. C57BL.6 mice express the LY5.2 allele, while the B6:PL Thy-1$^a$ mice express the Ly5.1 allele.

Splenocytes from LY5.1 B6:PL Thy-1$^a$) mice were activated as previously described. Briefly, purified splenocytes were cultured in tissue culture media (TMC) containing 3% volume:volume of the supernatant from the 145-2C11 hybridoma (Hamster anti-mouse anti-CD3 MoAb) for a period of 18 hours. The activated cells were then injected intravenously into LY5.2 (C57BL.6) mice. These mice also received intraperitoneal (i.p.) IL-2-liposomes (OncoTherapeutics Inc.) at a dose of 50,000 units once a day i.p. for 5 days. Mice were sacrificed on days 2 and 10 after injection at which time the following parameters were measured:

1. Percent CD4+ and CD8+ lymphocytes.
2. Percent T cells expressing the IL-2 receptor (TAC+ as a sign of activation.)
3. The percentage of LY5.1 cells in the spleen.
4. The number of white blood cells in the peripheral blood and spleen.

On day 0 (after stimulation of LY5.1 cells with anti-CD3, but prior to infusion) the T cells (CD4 and CD8) in the stimulated culture expressed an increased level of IL-2 receptor (78 and 92%) (Table 4). This is an increase from baseline which usually is $\leq 10\%$ in a normal unstimulated animal. As observed, the percentage of CD8+ cells increased in vivo over time while the CD4+ cells decreased. The number of LY5.1 cells in the spleen of the LY5.2 recipient animal increased over time until day 10 where 34% of the spleen cells were of .LY5.1 origin, confirming their expansion in vivo. In addition, the number of white blood cells in the peripheral blood increased dramatically to 88,000/mm$^3$. This data confirms the in vivo proliferation of cells activated in vitro with anti-CD3.

TABLE 4

In Vivo Growth of Anti-CD3 Stimulated Splenocytes
(Donor Ly 5.1+, Recipient Ly 5.2+)

| Day After Transfer | % Positive CD4(TAC+) | CD8(TAC+) | % Ly 5.1 in Spleen | Peripheral Blood WBC × 1000 |
|---|---|---|---|---|
| 0 | 23(78) | 18(92) | — | 2 |
| 2 | 17(21) | 53(38) | 15 | 3 |
| 10 | 11(3) | 63(3) | 34 | 88 |

EXAMPLE 9

Regression of Tumor Size After Treatment With Anti-CD3 Stimulated Cells and IL-2 Liposomes Murine lymphocytes stimulated overnight induce a significant reduction in the volume of subcutaneous tumors in mice bearing the MCA-38 colon carcinoma (Table 5). 500,000 MCA-38 tumor cells were injected subcutaneously into mice. After 10–15 days a nodule could be palpated at the site. These mice were injected with anti-CD3 stimulated murine splenocytes (using the same technique described in Table 4) and 50,000 U/day of i.p. IL-2 liposomes. Tumor measurements were performed every other day. The data presented in Table 5 demonstrate that only one out of ten mice receiving IL-2-liposomes with T-AK cells had tumor progressively grow while nine out of ten had complete tumor regression. Instead, all the mice in the groups receiving no therapy and 50% of the mice receiving IL-2 liposomes +CYTOXAN developed tumors which progressively increased in size.

TABLE 5

| Group | Day | 28 | 31 | 35 | 41 |
|---|---|---|---|---|---|
| | | Tumor Volume in mm³ | | | |
| Ia-Control (HRSS) | | | | | |
| | 1 | ++ | | | |
| | 2 | 7260 | 11492 | ++ | |
| | 3 | 8750 | 6800 | 10656 | ++ |
| | 4 | 7986 | ++ | | |
| | 5 | 1296 | 8064 | 5800 | 15558 |
| IIa-Cytoxad + IL-2 liposomes | | | | | |
| | 1 | 172 | 787 | 3971 | 7488 |
| | 2 | 0 | 0 | 0 | 6 |
| | 3 | 144 | 550 | 847 | 3726 |
| | 4 | 0 | 0 | 0 | 0 |
| | 5 | 0 | 0 | 0 | 0 |
| | 6 | 40 | 108 | 405 | 2916 |
| | 7 | 126 | 256 | 550 | 2916 |
| | 8 | 600 | 2746 | 3324 | 9802 |
| | 9 | 0 | 0 | 0 | 0 |
| | 10 | 0 | 0 | 0 | 0 |
| IIIa-Cytoxan + IL-2 liposomes + T-AK cells | | | | | |
| | 1 | 0 | 0 | 0 | 0 |
| | 2 | 0 | 0 | 0 | 0 |
| | 3 | 0 | 0 | 0 | 0 |
| | 4 | 0 | 0 | 0 | 0 |
| | 5 | 0 | 0 | 0 | 0 |
| | 6 | 0 | 0 | 0 | 0 |
| | 7 | 144 | 600 | 2156 | 7142 |
| | 8 | 0 | 0 | 0 | 0 |
| | 9 | 0 | 0 | 0 | 0 |
| | 10 | 0 | 0 | 0 | 0 |

TUMOR-MCA-38 (SQ)
DOSE OF CELLS: 10 M (1 dose)
IL-2-LIPOSOMES: 50 K/D × 5D

++ Mice sacrificed due to tumor growth

EXAMPLE 10

Increase in IL-2 Receptor Expression After Stimulation With Anti-CD3

Figure 2:
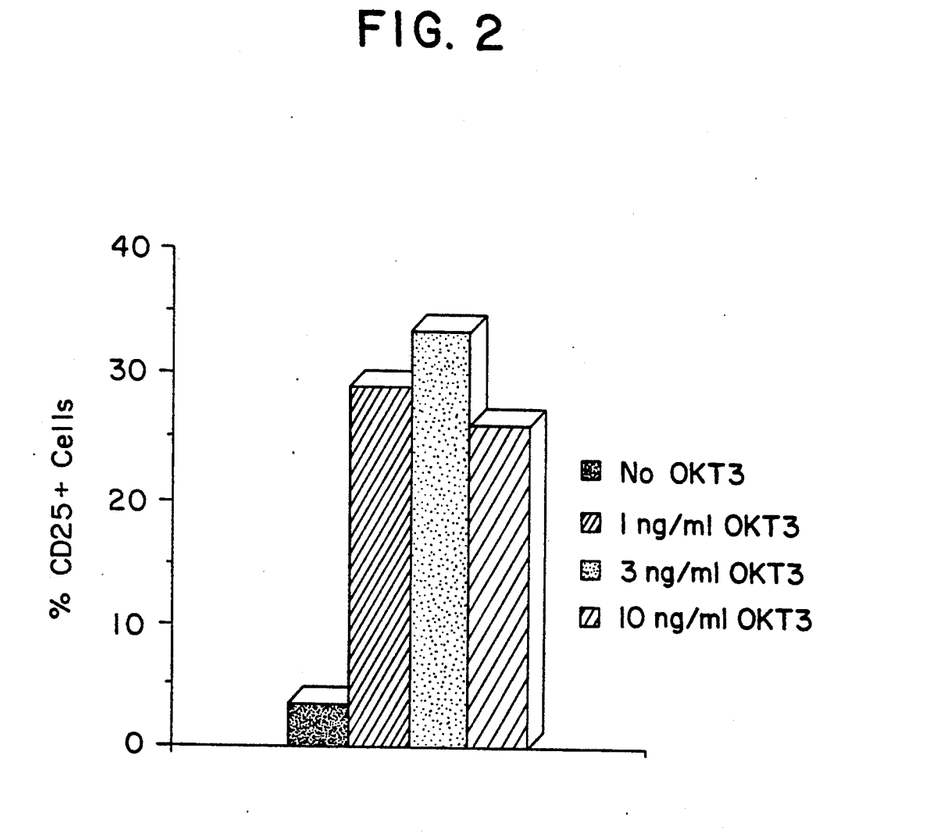
FIG. 2 shows the comparative increase of IL-2 receptors after 24 hours of stimulation in varying concentrations of anti-CD3.

IL-2 receptor (p55,CD25) is upregulated on human T lymphocytes after a 12 hour incubation with anti-CD3 (OKT3-Ortho) (FIG. 2). Lymphocytes were cultured as described above and the expression of the IL-2 receptor was measured by flow cytometry using a fluoresceinlabeled anti-CD25 MoAb against the p55 or $\beta$ chain of the the IL-2 receptor (Becton-Dickinson, Calif.). Human peripheral blood lymphocytes stimulated with doses as low as 1 ng/ml of OKT3 exhibited increased expression of the $\beta$ chain of the IL-2 receptor. Also, incubation with anti-CD3 for periods of time as short as 1 hour followed by 12 hours in TCM alone, also resulted in the increased expression of CD25.

Figure 3:
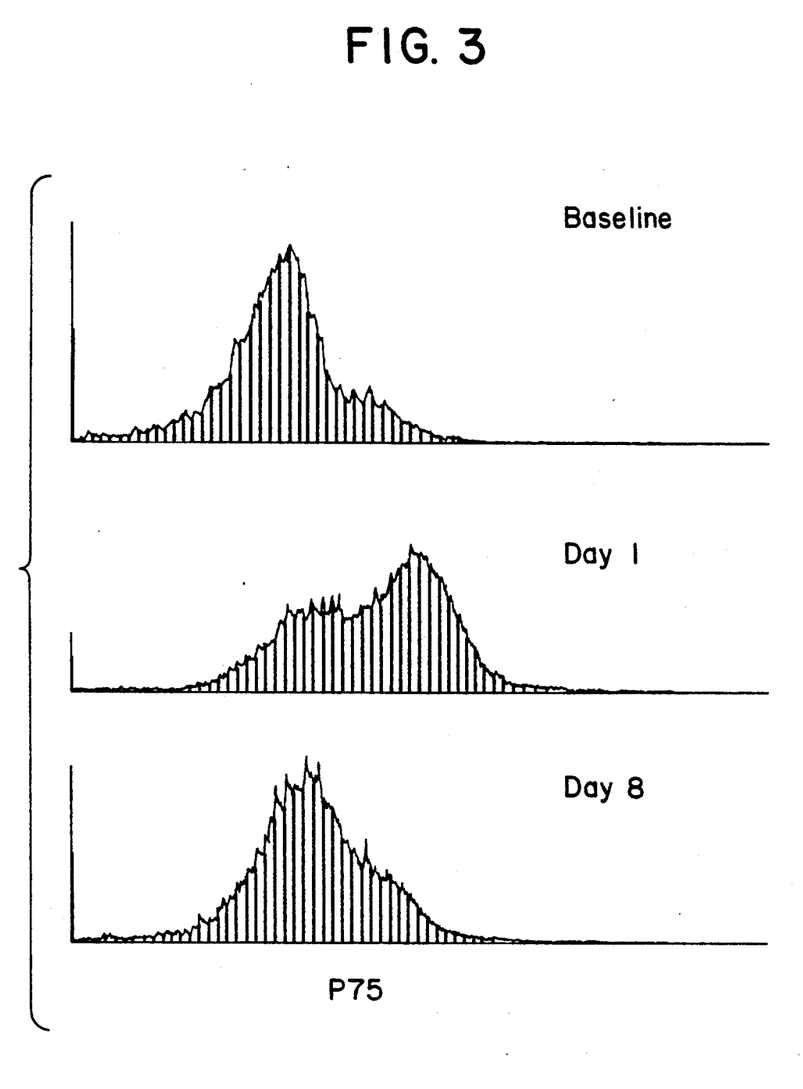
FIG. 3 shows the increase in the expression of the chain of the IL-2 receptor on human T lymphocytes after overnight incubation with anti-CD3.

Human T lymphocytes also increase their expression of the $\alpha$ chain (p75) of the IL-2 receptor after overnight incubation with anti-CD3 (FIG. 3). It is noted that the receptor itself has a high affinity for IL-2, as does the cell because it has so many receptors on it. The increased expression of both the $\alpha$ and $\beta$ chains makes the IL-2 receptor expressed by these T cells a receptor with very high affinity of IL-2.

EXAMPLE 11

In Vitro Proliferation of Human Lymphocytes Incubated with Anti-CD3

Figure 4:
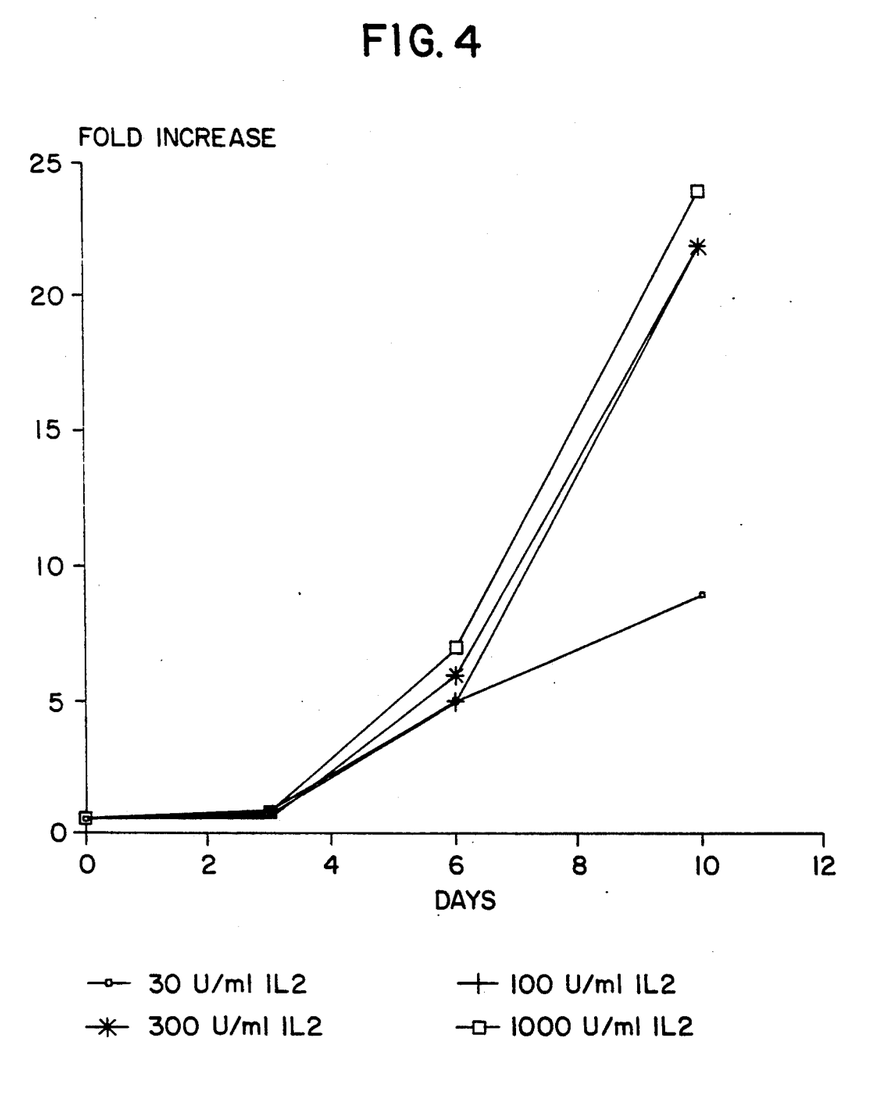
FIG. 4 shows human lymphocyte growth after 24 hour stimulation with anti-CD3 and subsequent culturing in media containing IL-2.

Human lymphocytes stimulated overnight with anti-CD3 proliferate when placed in media containing IL-2 (FIG. 4) Human lymphocytes at a concentration of $3 \times 10^6$ cells/ml were incubated with 10 ng/ml of OKT3 at 4° C. Cells were washed twice with HBSS and were placed in tissue culture media (TMC) composed of RPMI 1640 or AIM-V supplemented with 25 mM HEPES, 2 mM L-glutamine, 100 U/ml of penicillin, 100 $\mu$g/ml of streptomycin, 5% heat inactivated human AB serum (GIBCO) and 30, 100, 300, or 1000 units/ml of IL-2. Cells were counted on the days indicated and were diluted back to $0.5 \times 10^6$ cells/ml in fresh TCM. As observed, by day 10 the number of cells had increased between 20 and 25 fold.

EXAMPLE 12

OKT3 Induced Cell Proliferation

Figure 5:
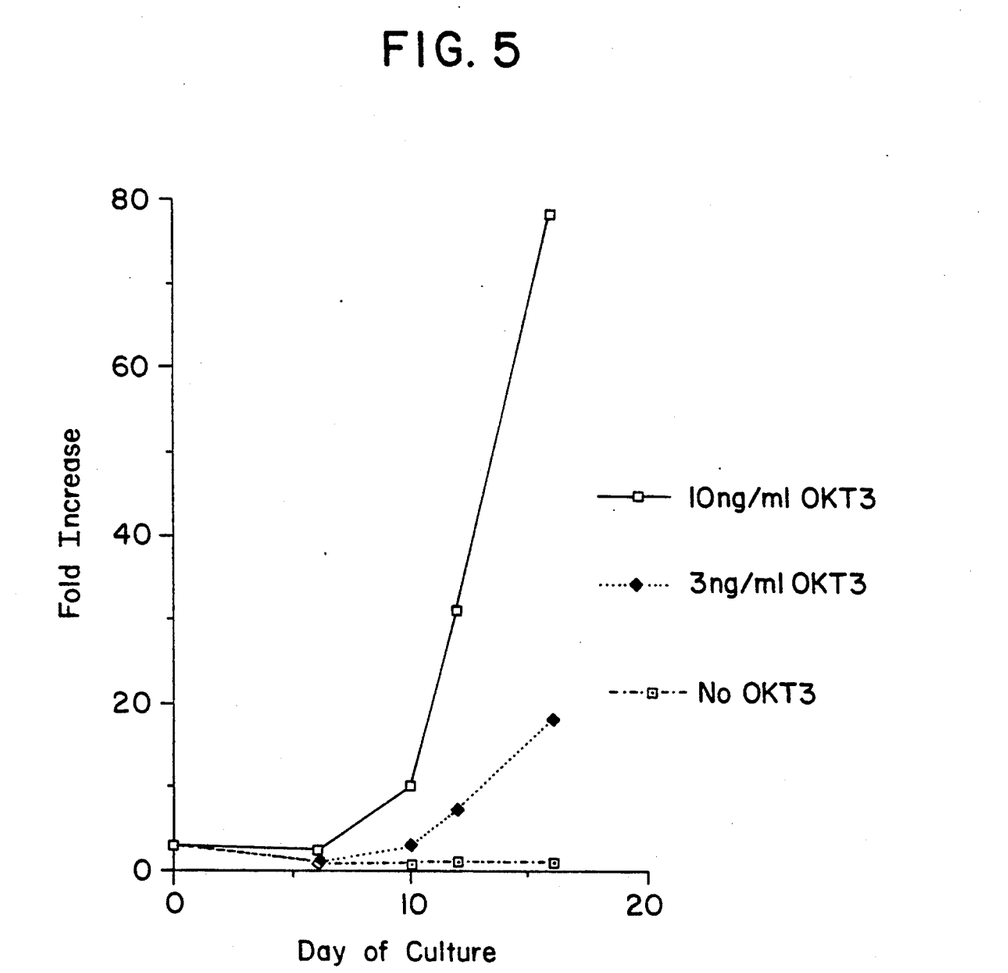
FIG. 5 shows the growth of lymphocytes stimulated with differing concentrations of anti-CD3 for four hours followed by culture in IL-2 containing medium.

Lymphocytes stimulated with anti-CD3 for as short as 4 hours will proliferate adequately in the presence of IL-2. Lymphocytes were cultured with no OKT3, or 3 or 10 ng/ml of OKT3 for 4 hours. Lymphocytes were washed twice with HBSS and then were cultured in tissue culture media containing 100 u/ml of IL-2. As shown in FIG. 5, either concentration of OKT3 tested induced cell proliferation.

EXAMPLE 13

In Vivo Proliferation of Human T Cells Treated With IL-2

Figure 6:
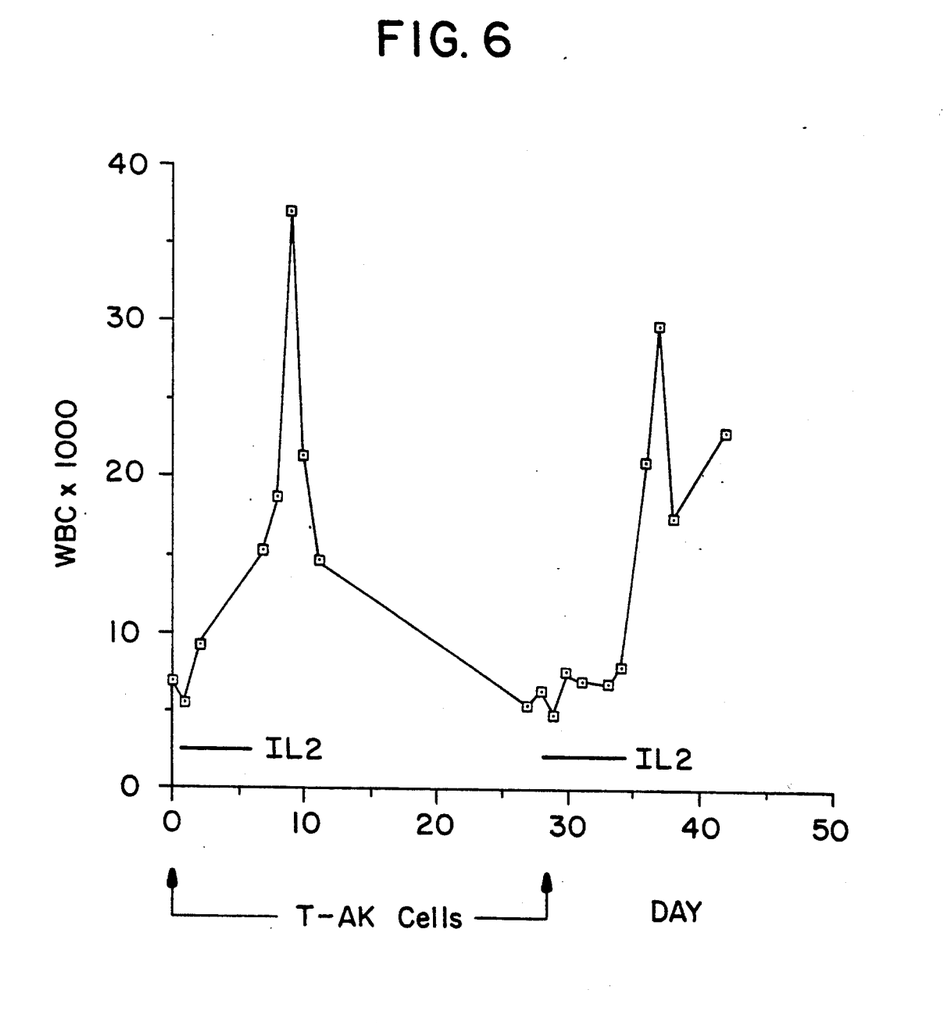
FIG. 6 shows the white blood cell count from a patient whose lymphocytes were cultured overnight in anti-CD3. The lymphocytes were infused back into the patient and the patient subsequently received IL-2 treatments.

Human T lymphocytes proliferate in vivo in cancer patients after receiving T-AK cells and IL-2. Patient lymphocytes were obtained by leukopheresis one day prior to the initiation of treatment (day-1). The cells were purified over Ficoll-Hypaque and cultured overnight at a concentration of $3 \times 10^6$ cells/ml in AIM-V media with 10 ng/ml of OKT3. After overnight culture, the cells were washed 3 times in HBSS, resuspended in reinfusion medium (0.9% saline solution (Abott Laboratories) containing 25% human serum albumin (American Red Cross) and 30 U/ml of IL-2) and given back to the patients by intravenous infusion over 30 minutes. The patients then received IL-2 intravenously (3 million U/m2 continuous infusion and 1.5 million U/m2 bolus for a total of 7 days (proliferation has also been observed with lower doses of IL-2 being administered). Samples of peripheral blood were obtained from the patient on the days presented in FIG. 6 and a WBC count and differential counts were done.

There was a marked increase in the WBC after 6-8 days in therapy. This increase was on the average 4-6 fold over the baseline number of WBC. The WBC ranged up to 86,000 per $mm^3$ in one patient. Only one patient out of 25 thus far has not shown any increase in peripheral WBC. This increase was preferential for the T cells (CD3+), although other cells including the NK cells (CD16+/CD56+) increased in absolute number (Table 6). The CD3+ T lymphocytes also had an increased expression of activation markers (Table 7) such as IL-2 receptor (CD25), HLA-Dr and CD38, demonstrating the presence of a large number of activated T cells in the circulation. Because of the similarity to the results obtained int he murine experiments, it is most likely that the cels proliferating in the peripheral blood are those which were stimulated with OKT3 in vitro. However, because of the genetic disparity of the patients, experiments to confirm this possibility definitively cannot be done.

TABLE 6

Cohort 2 - Surface Phenotype

| Relative Data | % Positive | | | |
|---|---|---|---|---|
| | CD3 | CD4 | CD8 | CD56 |
| Baseline | 76 | 49 | 28 | 10 |
| Day 1 Culture | 75 | 53 | 30 | 7 |
| Day 7-9 | 83 | 39 | 43 | 16 |
| Day 28 | 88 | 56 | 31 | 9 |
| Day 29 Culture | 84 | 57 | 31 | 6 |
| Day 35-37 | 82 | 50 | 32 | 16 |

TABLE 7

Cohort 2 - Surface Phenotypes

| Relative Date | % CD3+ Cells | | | |
|---|---|---|---|---|
| | HLA-DR | CD25 | CD38 | CD69 |
| Baseline | 4 | 6 | 31 | 3 |
| Day 1 Culture | 11 | 12 | 33 | 51 |
| Day 7-9 | 55 | 31 | 82 | 7 |
| Day 28 | 8 | 18 | 25 | 3 |
| Day 29 Culture | 17 | 32 | 26 | 50 |
| Day 35-37 | 41 | 42 | 64 | 6 |

EXAMPLE 14

Lymphocytic Infiltration of Tumors

Figure 7B:
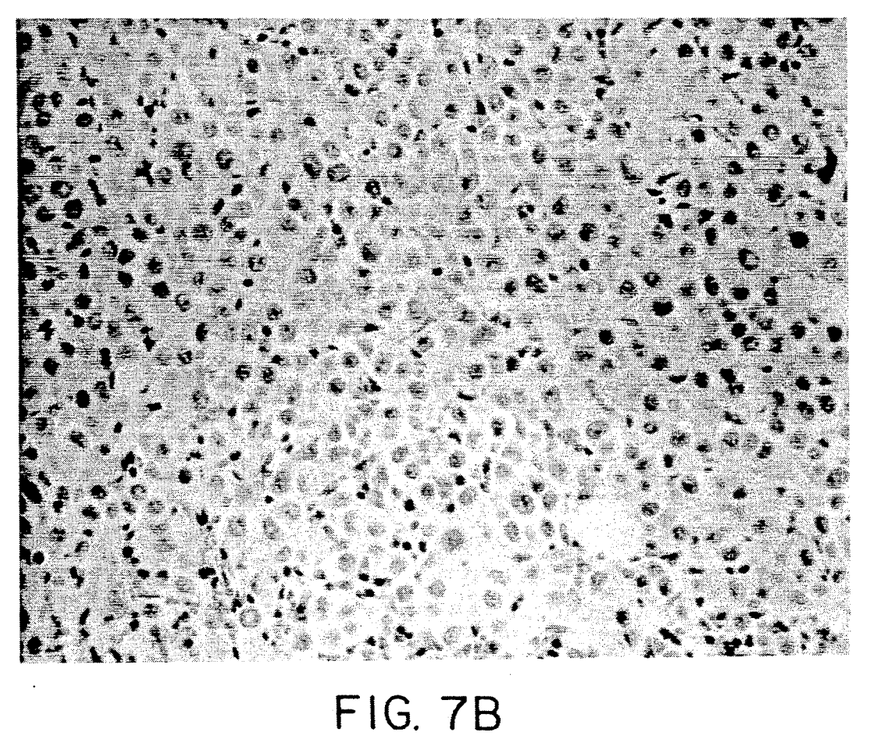
FIG. 7 illustrates the infiltration of T-AK lymphocytes into tumor. Print A shows a melanoma biopsy prior to T-AK therapy. The print shows a homogeneous sheet of melanoma cells with occasional mononuclear cells interspersed. Print B shows a biopsy from the same patient after receiving one 7 day cycle of T-AK cells and IL-2. The tumor cells are surrounded by a large infiltrate of mononuclear cells.

CD8+ cells infiltrate the site of tumor. In two patients in which tumor biopsies were obtained, a significant lymphocytic infiltration was observed as compared with the pre-treatment biopsy. (FIG. 7) Further analysis using well-established, routine techniques of immunohistology revealed that these cells were mostly CD8+ cells.

The invention has been described with reference to various specific and preferred embodiments and techniques. However, it should be understood that many variations and modifications may be made while remaining within the spirit and scope of the invention. The relevant portions of the references cited herein are incorporated by reference.

What is claimed is:

1. A method of enhancing the in vivo immunotherapeutic activity of lymphocytes comprising:
    (a) stimulating the lymphocytes in vitro by means of culturing said lymphocytes with an anti-CD3 monoclonal antibody for less than about 24 hours, optionally in the presence of interleukin-2 (IL-2), to form stimulated lymphocytes;
    (b) infusing the stimulated lymphocytes into a tumor-bearing mammal, wherein said stimulated lymphocytes are infused into said mammal without substantial further in vitro culture; and
    (c) administering an amount of IL-2 to the mammal effective to induce proliferation of said stimulated lymphocytes in vivo; whereby the immunotherapeutic activity of the lymphocytes is enhanced in vivo, resulting in a decrease in the tumor burden by at least about 20%.

2. The method of claim 1 wherein the step of stimulating in the presence of anti-CD3 is carried out for about 12-18 hours.

3. The method of claim 1, wherein in step (c), the IL-2 is administered encapsulated in liposomes.

4. The method of claim 1 wherein the tumor burden is decreased by at least about 40%.

5. The method of claim 1 wherein the tumor burden is decreased by at least about 60%.

6. The method of claim 1 wherein the tumor burden is decreased by at least about 80%.

7. The method of claim 1 wherein the tumor-bearing mammal is a human.

8. The method of claim 7, wherein in step (c), the IL-2 is administered in about 3 million $U/m^2$ continuous infusion and 1.5 million $U/m^2$ bolus per day.

9. The method of claim 7, wherein step (a) includes stimulating in the presence of less than 300 units/ml of IL-2.

10. The method of claim 8, wherein step (a) includes stimulating in the presence of less than 300 units/ml of IL-2.

11. The method of claim 1, wherein step (a), said culturing is effected in the substantial absence of IL-2.

12. The method of claim 7, wherein step (c), the IL-2 is administered encapsulated in liposomes.

13. The method of claim 8, wherein step (c), the IL-2 is administered encapsulated in liposomes.

14. The method of claim 7, wherein step (a), said culturing is effected for 30 minutes to less than about 4 hours.

15. The method of claim 14, wherein step (c), the IL-2 is administered encapsulated in liposomes.

16. The method of claim 11, wherein step (c), the IL-2 is administered encapsulated in liposomes.

* * * * *